US012575704B2

(12) United States Patent (10) Patent No.: US 12,575,704 B2
Clement et al. (45) Date of Patent: Mar. 17, 2026

(54) AIR PURIFICATION DEVICE

(71) Applicants: Clarence Clement, Raceland, LA (US);
Erica Clement, Raceland, LA (US)

(72) Inventors: Clarence Clement, Raceland, LA (US);
Erica Clement, Raceland, LA (US)

( * ) Notice: Subject to any disclaimer, the term of this
patent is extended or adjusted under 35
U.S.C. 154(b) by 562 days.

(21) Appl. No.: 18/074,221

(22) Filed: Dec. 2, 2022

(65) Prior Publication Data

US 2023/0098771 A1 Mar. 30, 2023

Related U.S. Application Data

(63) Continuation-in-part of application No. 16/591,775,
filed on Oct. 3, 2019, now abandoned.

(51) Int. Cl.
*B01D 53/04* (2006.01)
*A47K 13/30* (2006.01)
*A61L 9/014* (2006.01)

(52) U.S. Cl.
CPC ............. *A47K 13/307* (2013.01); *A61L 9/014*
(2013.01); *A61L 2209/14* (2013.01); *A61L*
*2209/22* (2013.01)

(58) Field of Classification Search
CPC ... A47K 13/307; A61L 9/014; A61L 2209/14;
A61L 2209/22; A61L 2209/111; E03D
9/007; E03D 9/052; E03D 9/05; B01D
2257/90; B01D 2258/06; B01D
2259/4508; B01D 53/0407; B01D
53/0446; B01D 53/04
USPC ........... 96/108, 147, 222; 422/5, 120; 4/213,
4/217
See application file for complete search history.

(56) References Cited

U.S. PATENT DOCUMENTS 1,798,457 A * 3/1931 Cole ....................... E03D 9/052
4/213
4,375,704 A 3/1983 Smith
5,231,705 A * 8/1993 Ragusa .................... E03D 9/05
4/348
5,829,066 A * 11/1998 Aibe ....................... E03D 9/052
4/213
5,850,638 A 12/1998 Her
6,003,157 A * 12/1999 Bruyere ................. E03D 9/052
15/327.6
6,041,449 A 3/2000 Brown
6,233,750 B1 * 5/2001 Donald .................. E03D 9/007
4/213
6,363,542 B1 4/2002 Pope, Sr.
(Continued)

FOREIGN PATENT DOCUMENTS

WO WO2008002519 1/2008

*Primary Examiner* — Frank M Lawrence, Jr.

(57) ABSTRACT

An air purification device for maintaining a clean smelling
bathroom includes a housing, which is mountable to a tank
of a toilet, and a plurality of bulbs, which is mountable to an
underside of a seat of the toilet. An opening is positioned in
the housing to vent the housing. A tube is attached to and
extends from the housing to a bowl of the toilet. A battery,
a pump, and a filter are attached to and positioned in the
housing. The battery is operationally engaged to the pump
and the bulbs, positioning the bulbs to selectively illuminate
an area proximate to the toilet. The pump draws air from the
bowl through the tube into the housing, where the filter
absorbs malodorous compounds in the air to purify the air,
thus maintaining a clean smell in proximity to the toilet.

13 Claims, 4 Drawing Sheets

(56)                References Cited

U.S. PATENT DOCUMENTS

| | | | |
|---|---|---|---|
| D461,547 S | 8/2002 | Christian, Sr. | |
| 6,678,900 B2 | 1/2004 | Ware | |
| 7,797,766 B2 | 9/2010 | Ellinger | |
| 7,823,227 B2 | 11/2010 | Damianoe | |
| 8,337,602 B2 | 12/2012 | Foerster | |
| 2006/0277671 A1 | 12/2006 | Jones | |
| 2007/0256219 A1 | 11/2007 | Ellinger | |
| 2008/0040842 A1 | 2/2008 | Sanabria | |
| 2008/0060119 A1 | 3/2008 | Pinizzotto | |
| 2009/0158575 A1* | 6/2009 | Currie ..................... | B29C 35/02 |
| | | | 29/428 |
| 2014/0304903 A1* | 10/2014 | Cogswell ................ | E03D 9/052 |
| | | | 4/314 |
| 2019/0360186 A1* | 11/2019 | Foss ......................... | E03D 9/032 |

* cited by examiner

AIR PURIFICATION DEVICE

CROSS-REFERENCE TO RELATED APPLICATIONS

This application is a continuation in part of U.S. application Ser. No. 16/591,775 filed on Oct. 3, 2019 and claims the benefit thereof under Title 35, United States Code, Section 120.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to purification devices and more particularly pertains to a new purification device for maintaining a clean smelling bathroom. The present invention discloses a purification device that filters and freshens air drawn from a bowl of a toilet and which illuminates an area proximate to the toilet.

(2) Description of Related Art Including Information Disclosed Under 37 CFR 1.97 and 1.98

The prior art relates to purification devices. The prior art does not disclose a purification device that filters and freshens air drawn from a bowl of a toilet and which illuminates an area proximate to the toilet.

BRIEF SUMMARY OF THE INVENTION

An embodiment of the disclosure meets the needs presented above by generally comprising a housing and a plurality of bulbs. The housing defines an interior space and is configured to be mountable to a tank of a toilet so that the housing is mounted to the tank. The bulbs are configured to be mountable to an underside of a seat of the toilet. An opening that is positioned in the housing is configured to vent the interior space. A tube is attached to and extends from the housing to a bowl of the toilet. A battery, a pump, and a filter are attached to the housing and are positioned in the interior space. The battery is operationally engaged to the pump and the bulbs, positioning the bulbs to selectively illuminate an area proximate to the toilet and the pump to draw air from the bowl through the tube. The filter is configured to absorb malodorous compounds in the air to purify the air to maintain a clean smell in proximity to the toilet.

Another embodiment of the disclosure includes an air purification system, which comprises an air purification device, as described in the disclosure above, which is mounted to a toilet.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
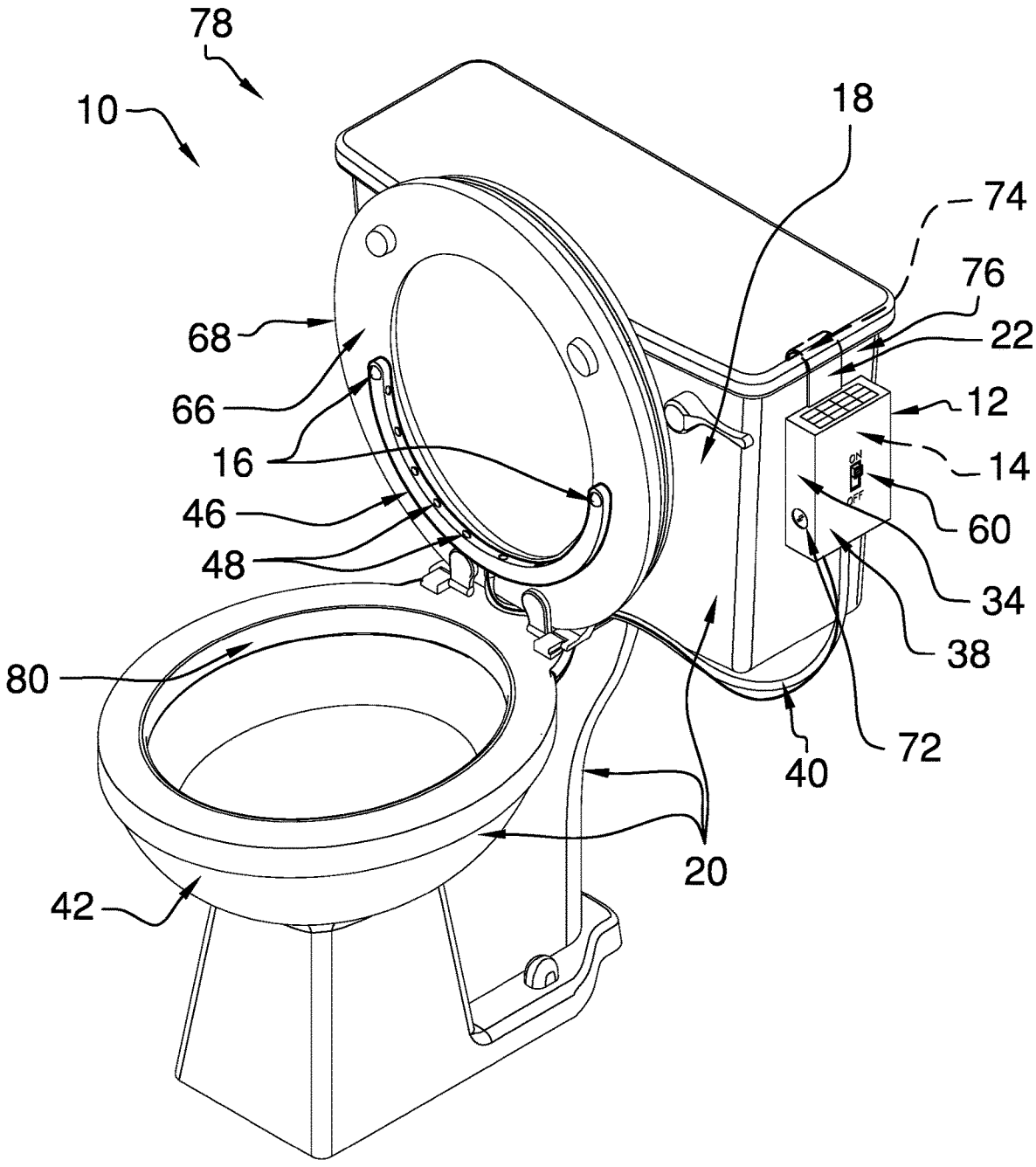
FIG. 1 is an isometric perspective view of an air purification device according to an embodiment of the disclosure.

With reference now to the drawings, and in particular to FIGS. 1 through 4 thereof, a new purification device embodying the principles and concepts of an embodiment of the disclosure and generally designated by the reference numeral 10 will be described.

As best illustrated in FIGS. 1 through 4, the air purification device 10 generally comprises a housing 12, which defines an interior space 14 and which is configured to be mountable to a tank 18 of a toilet 20 so that the housing 12 is attached to the tank 18. The housing 12 may be substantially rectangularly box shaped, or may be alternatively shaped, such as, but not limited to, tubularly shaped, disc shaped, and the like. The air purification device 10 also comprises a plurality of bulbs 16, which is configured to be mountable to an underside 66 of a seat 68 of the toilet 20.

Figure 4:
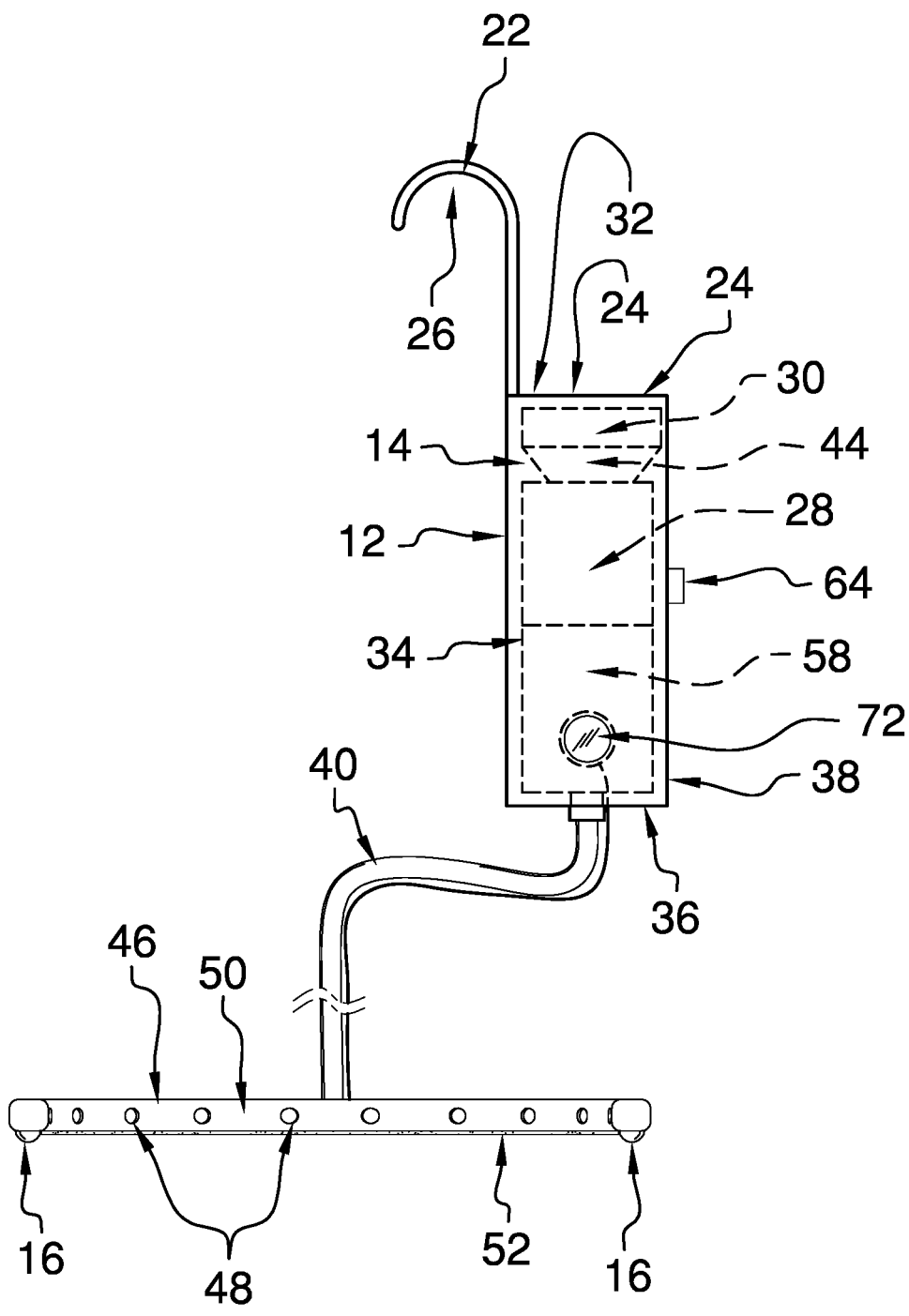
FIG. 4 is a side view of an embodiment of the disclosure.

A hook 22 is attached to and extends from a top 24 of the housing 12, as shown in FIG. 4. A gap 26 of the hook 22 is configured to insert a rim 74 of a wall 76 of the tank 18 so that the housing 12 is suspended from the tank 18. Other coupling means, such as, but not limited to, adhesives, suction cups, and the like, may be used in mounting the housing 12 to the tank 18

Figure 3:
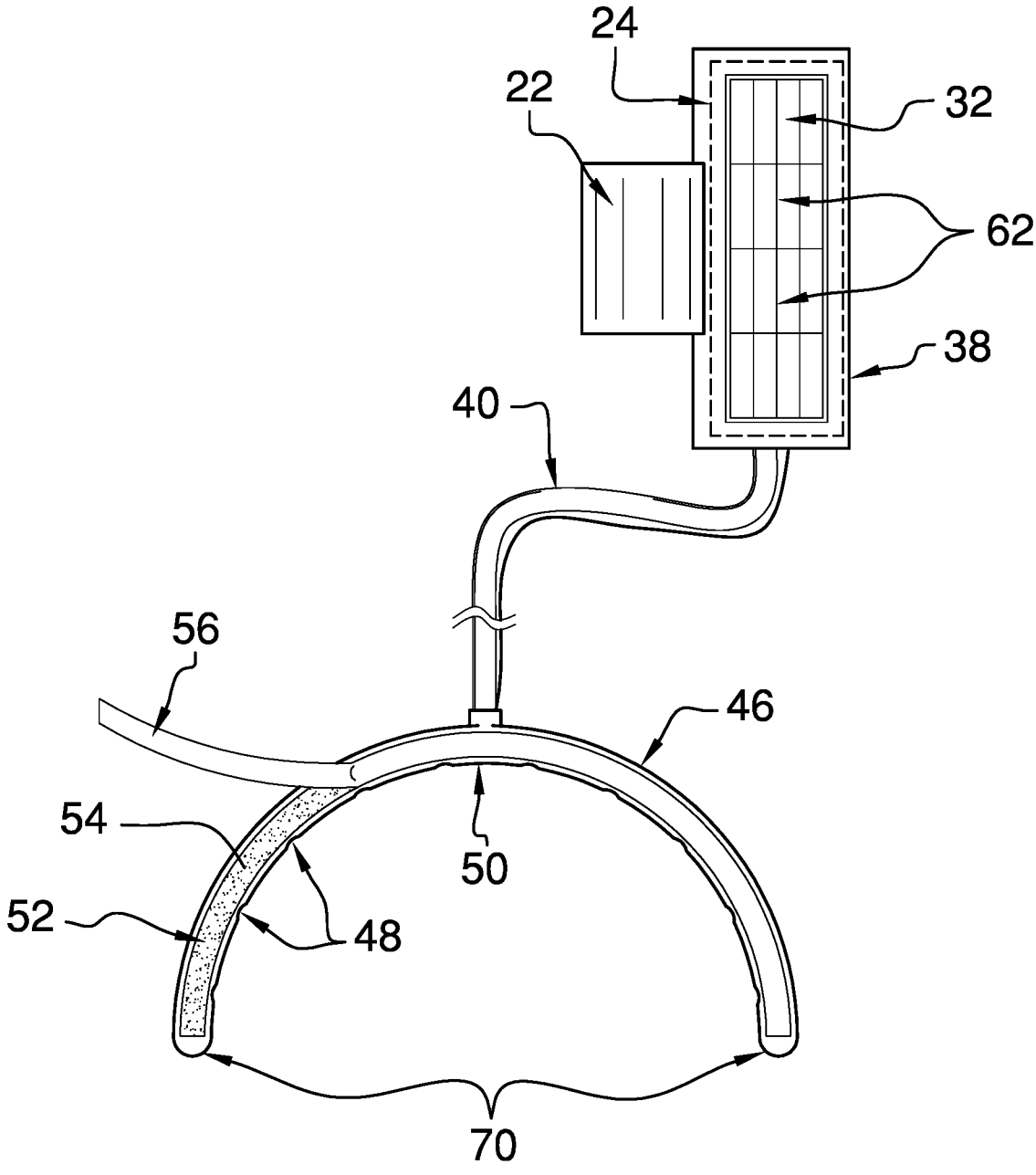
FIG. 3 is a top view of an embodiment of the disclosure.

A pump 28, a filter 30, and a battery 58 are attached to the housing 12 and are positioned in the interior space 14. The filter 30 is operationally engaged to the pump 28. The battery 58 is operationally engaged to the pump 28 and to the plurality of bulbs 16 and thus is positioned to selectively power the pump 28 and the bulbs 16. The bulbs 16 are configured to illuminate an area proximate to the toilet. An opening 32 that is positioned in the housing 12 is configured to vent the interior space 14. The opening 32 may be positioned in the top 24 of the housing 12, as shown in FIG. 3, or may be positioned in a side 34, bottom 36, or front 38 of the housing 12. The opening 32 may be rectangularly shaped, or may be alternatively shaped, such as, but not limited to, ovally shaped, circularly shaped, and the like.

A tube 40 is attached to and extends from the housing 12 to a bowl 42 of the toilet 20, as shown in FIG. 1. The pump 28 is configured to draw air from the bowl 42 through the tube 40. The filter 30 is configured to absorb malodorous compounds in the air to purify the air. The filter 30 comprises at least one of activated charcoal, silica, and zeolite and thus is configured to absorb the malodorous compounds in the air to purify the air. The filter 30 also is permeated with an aroma compound 44 so that the filter 30 is configured to release the aroma compound 44 into the air that passes through the filter 30 to freshen the air.

The filter 30 may be positioned between the pump 28 and the opening 32, as shown in FIG. 4, so that the air is pushed through the filter 30. Although not shown in the figures, the filter 30 also may be positioned between the pump 28 and the tube 40 so that the air is drawn through the filter 30.

Figure 2:
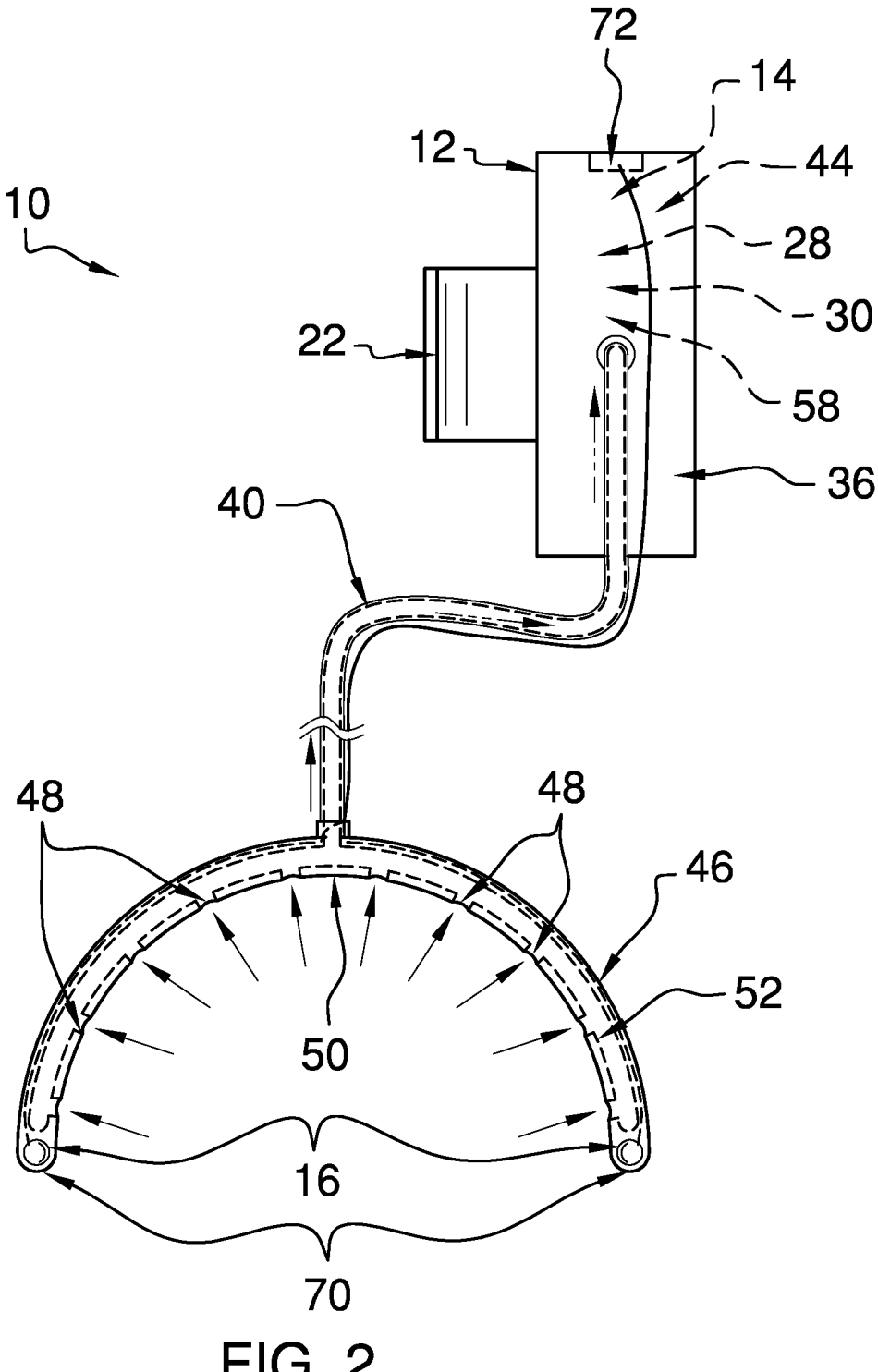
FIG. 2 is a bottom view of an embodiment of the disclosure.

A pipe 46 is attached to and extends bidirectionally from the tube 40 distally from the pump 28, as shown in FIG. 2. The pipe 46 is arcuate so that the pipe 46 is shaped complementarily to the seat 68 of the toilet 20. A plurality of apertures 48 that is positioned in an inner perimeter 50 of the pipe 46 is configured for entry of air from the bowl 42 of the toilet 20 into the pipe 46. The plurality of bulbs 16 is attached to the pipe 46 and may comprises two bulbs 16, with each bulb 16 being attached to the pipe 46 proximate to a respective opposed end 70 of pipe 46. The present invention also anticipates the plurality of bulbs 16 comprising more than two bulbs 16.

A fastener 52 that is attached to the pipe 46 is configured to selectively couple to the seat 68 of the toilet 20 to couple the pipe 46 to the seat 68 of the toilet 20. Alternatively, the fastener 52 can be used to couple the pipe 46 to a lip 80 of the bowl 42. The fastener 52 may comprise an adhesive 54, as shown in FIG. 3, or other fastening means, such as, but not limited to, hook and loop fasteners, clips, and the like. A strip 56 that is selectively couplable to the adhesive 54 is configured to prevent inadvertent adhesion of the adhesive 54. The strip 56 is configured to be decoupled from the adhesive 54, positioning the adhesive 54 to couple the pipe 46 to the seat 68 of the toilet 20.

A switch 60, which is attached to the housing 12, is operationally coupled to the battery 58 and to one or both of the plurality of bulbs 16, and the pump 28. The switch 60 is configured to be switched to selectively couple one or both of the bulbs 16 and the pump 28 to the battery 58. The switch 60 may comprise a slide switch 64, as shown in FIG. 4, or other switching means, such as, but not limited to, toggles, push buttons, and the like.

A grate 62 is selectively couplable to the housing 12 to screen the opening 32, as shown in FIG. 3. The grate 62 is configured to be removed from the housing 12 to access the interior space 14 to service the pump 28, the filter 30, and the battery 58.

A sensor 72 is attached to the housing 12 and is operationally engaged to the battery 58 and to one or both of the pump 28 and the bulbs 16. The sensor 72 is configured to detect motion of a user proximate to the toilet 20, positioning the battery 58 to selectively power the bulbs 16 to illuminate the area proximate to the toilet 20 and to power the pump 28 to draw air from the bowl 42 through the tube 40, respectively. Such electronics assemblies are well known to those skilled in the art of sensed device controllers and can include selectors allowing a user to select modes of operations, which may include actuating, upon detection of motion by the sensor 72, only the bulbs 16, only the pump 28, or both the bulbs 16 and the pump 28.

The present invention also anticipates an air purification system 78, as shown in FIG. 1, which comprises an air purification device 10, as described in the disclosure above, which is mounted to a toilet 20.

In one example of use, a user enters a bathroom and motion is detected by the sensor 72, whereupon the battery 58 powers the bulbs 16 to illuminate the area proximate to the toilet 20. The user switches the switch 60 and the pump 28 draws the air from the bowl 42 and pushes the air through the filter 30, which absorbs the malodorous compounds in the air and releases the aroma compound 44 so that the air is both purified and freshened before exiting the housing 12 through the opening 32.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

We claim:

1. An air purification device comprising:
a housing defining an interior space and configured to be mountable to a tank of a toilet, such that the housing is mounted to the tank;
a pump attached to the housing and positioned in the interior space;
an opening positioned in the housing, wherein the opening is configured for venting the interior space;
a filter coupled to the housing, positioned in the interior space, and operationally engaged to the pump; and
a tube configured to be attached to and extending from the housing to a bowl of the toilet;
a plurality of bulbs configured to be mountable to an underside of a seat of the toilet;
a battery attached to the housing and positioned in the interior space, the battery being operationally coupled to the pump and the plurality of bulbs, such that the battery is positioned for selectively powering the pump and the bulbs, wherein the pump is configured for drawing air from the bowl through the tube, wherein the filter is configured for absorbing malodorous compounds in the air for purifying the air, and wherein the bulbs are configured for illuminating an area proximate to the toilet;

a pipe coupled to and extending bidirectionally from the tube distal from the pump, the pipe being arcuate such that the pipe is shaped complementarily to the seat of the toilet, the bulbs being attached to the pipe;

a fastener coupled to the pipe, the fastener being configured for selectively coupling to the seat of the toilet wherein the fastener is configured for coupling the pipe to the seat of the toilet;

a plurality of apertures positioned in an inner perimeter of the pipe wherein the apertures are configured for entering of air from the bowl of the toilet into the pipe; and wherein the plurality of bulbs comprises two bulbs, each bulb being attached to the pipe proximate to a respective opposed end of pipe.

2. The air purification device of claim 1, further including a hook coupled to and extending from a top of the housing wherein a gap of the hook is configured for insertion of a rim of a wall of the tank such that the housing is suspended from the tank.

3. The air purification device of claim 1, further including the opening being positioned in a top of the housing.

4. The air purification device of claim 1, further comprising:

the housing being substantially rectangularly box shaped; and the opening being rectangularly shaped.

5. The air purification device of claim 1, further including the filter being positioned between the pump and the opening.

6. The air purification device of claim 1, further including the filter comprising at least one of activated charcoal, silica, and zeolite, wherein the filter is configured for absorbing the malodorous compounds in the air for purifying the air.

7. The air purification device of claim 1, further including the filter being permeated with an aroma compound, wherein the filter is configured for releasing the aroma compound into the air passing through the filter for freshening the air.

8. The air purification device of claim 1, further comprising:

the fastener comprising an adhesive; and a strip selectively couplable to the adhesive wherein the strip is configured for preventing inadvertent adhesion of the adhesive and for being decoupled from the adhesive positioning the adhesive for coupling the pipe to the seat of the toilet.

9. The air purification device of claim 1, further including a switch coupled to the housing, the switch being operationally coupled to the battery, the bulbs, and the pump, wherein the switch is configured for being switched for selectively coupling the pump and the bulbs to the battery.

10. The air purification device of claim 9, further including the switch comprising a slide switch.

11. The air purification device of claim 1, further including a grate selectively couplable to the housing for screening the opening wherein the grate is configured for being removed from the housing for accessing the interior space for servicing the pump, the filter, and the battery.

12. The air purification device of claim 1, further including a sensor attached to the housing and operationally engaged to one or both of the plurality of bulbs and the battery, the sensor being configured for detecting motion proximate to the toilet, wherein the sensor is configured for detecting motion of a user, positioning the battery for selectively actuating one or both of the bulbs and the pump for illuminating the area proximate to the toilet and for drawing air from the bowl through the tube, respectively.

13. An air purification device comprising:

a housing defining an interior space and being configured to be mountable to a tank of a toilet, such that the housing is mounted to the tank, the housing being substantially rectangularly box shaped;

a hook coupled to and extending from a top of the housing wherein a gap of the hook is configured for insertion of a rim of a wall of the tank such that the housing is suspended from the tank;

a pump attached to the housing and positioned in the interior space;

a plurality of bulbs configured to be mountable to an underside of a seat of the toilet, the plurality of bulbs comprising two bulbs;

an opening positioned in the housing, wherein the opening is configured for venting the interior space, the opening being positioned in the top of the housing, the opening being rectangularly shaped;

a filter coupled to the housing and positioned in the interior space, the filter being positioned between the pump and the opening, the filter being permeated with an aroma compound;

a tube configured to be attached to and extending from the housing to a bowl of the toilet wherein the pump is configured for drawing air from the bowl through the tube wherein the filter is configured for absorbing malodorous compounds in the air for purifying the air and for releasing the aroma compound into the air passing through the filter for freshening the air;

a battery attached to the housing and positioned in the interior space, the battery being operationally coupled to the pump and the plurality of bulbs, such that the battery is positioned for selectively powering the pump and the bulbs, wherein the pump is configured for drawing air from the bowl through the tube, and wherein the bulbs are configured for illuminating an area proximate to the toilet;

a sensor attached to the housing and operationally engaged to one or both of the plurality of bulbs and the battery, the sensor being configured for detecting motion proximate to the toilet, wherein the sensor is configured for detecting motion of a user, positioning the battery for selectively actuating one or both of the bulbs and the pump for illuminating the area proximate to the toilet and for drawing air from the bowl through the tube, respectively;

a pipe coupled to and extending bidirectionally from the tube distal from the pump, the pipe being arcuate such that the pipe is shaped complementarily to a seat of the toilet, the bulbs being attached to the pipe, each bulb being attached to the pipe proximate to a respective opposed end of pipe;

a fastener coupled to the pipe, the fastener being configured for selectively coupling to the seat of the toilet wherein the fastener is configured for coupling the pipe to the seat of the toilet, the fastener comprising an adhesive;

a strip selectively couplable to the adhesive wherein the strip is configured for preventing inadvertent adhesion of the adhesive and for being decoupled from the adhesive positioning the adhesive for coupling the pipe to the seat of the toilet;

a plurality of apertures positioned in an inner perimeter of the pipe wherein the apertures are configured for entering of air from the bowl of the toilet into the pipe;

a switch coupled to the housing, the switch being operationally coupled to the battery, the bulbs, and the pump, wherein the switch is configured for being switched for selectively coupling the bulbs and the pump to the battery, the switch comprising a slide switch; and a grate selectively couplable to the housing for screening the opening wherein the grate is configured for being removed from the housing for accessing the interior space for servicing the pump, the filter, and the battery.

* * * * *